US008183365B2

(12) United States Patent
Coleman et al.

(10) Patent No.: US 8,183,365 B2
(45) Date of Patent: May 22, 2012

(54) SYNTHETIC METHOD FOR CERATAMINE A AND B AND ANALOGS THEREOF

(75) Inventors: Robert S. Coleman, Bexley, OH (US); Erica L. Campbell, Livermore, CA (US); Daniel J. Carper, Columbus, OH (US)

(73) Assignee: The Ohio State University, Columbus, OH (US)

( * ) Notice: Subject to any disclaimer, the term of this patent is extended or adjusted under 35 U.S.C. 154(b) by 258 days.

(21) Appl. No.: 12/721,886

(22) Filed: Mar. 11, 2010

(65) Prior Publication Data
US 2010/0234588 A1     Sep. 16, 2010

Related U.S. Application Data

(60) Provisional application No. 61/159,108, filed on Mar. 11, 2009.

(51) Int. Cl.
*C07D 498/04* (2006.01)
(52) U.S. Cl. ...................................................... 540/521
(58) Field of Classification Search .................... 540/521
See application file for complete search history.

(56) References Cited

U.S. PATENT DOCUMENTS
2008/0255090 A1    10/2008   Andersen et al.

OTHER PUBLICATIONS

Emiliano Manzo, Rob Van Soest, Lohi Matainaho, Michel Roberge, and Raymond J. Andersen; Ceratamines A and B, Antimitotic Heterocyclic Alkaloids Isolated from the Marine Sponge *Pseudoceratina* sp. Collected in Papua New Guinea; Organic Letters 2003; Received Sep. 8, 2003; vol. 5, No. 24 4591-4594.
Geoffrey Karjala, Queenie Chan, Emiliano Manzo, Raymond J. Andersen, and Michel Roberge; Ceratamines, Structurally Simple Microtubule-Stabilizing Antimitotic Agents with Unusual Cellular Effects; Cancer Res 2005; Received Apr. 15, 2005; vol. 65, No. 8 pp. 3040-3043.
Anna Aiello, Ernesto Fattorusso, Marialuisa Menna, and Maurizio Pansini; Chemistry of Verongida Sponges -V.* Brominated Metabolites from the Caribbean Sponge *Pseudoceratina* sp.; Biochem. Syst. Ecol. 1995, vol. 23, pp. 377-381.
Piña, I. C.; Gautschi, J. T.; Wang, G.-Y.-S.; Sanders, M. L.; Schmitz, F. J.; France, D.; Cornell-Kennon, S.; Sambucetti, L. C.; Remiszewski, S. W.; Perez, L. B.; Bair, K. W.; Crews, P.; *Psammaplins* from the Sponge *Pseudoceratina purpurea*: Inhibition of Both Histone Deacetylase and DNA Methyltransferase; Journal of Organic Chemistry. 2003, vol. 68, pp. 3866-3873.
Keiko Hirano, Takaaki Kubota, Masashi Tsuda, Kenji Watanabe, Jane Fromont, and Jun'Ichi Kobayashi; Ma'edamines A and B, Cytotoxic Bromotyrosine Alkaloids with a Unique 2(1H)Pyrazinone Ring from Sponge *Suberea* sp.; Tetrahedron 2000, vol. 56, pp. 8107-8110.
Nodwell, M.; Pereira, A.; Riffell, J. L.; Zimmerman, C.; Patrick, B. O.; Roberge, M.; Andersen, R. J.; Synthetic Approaches to the Microtubule-Stabilizing Sponge Alkaloid Ceratamine A and Desbromo Analogues; Journal of Organic Chemistry. 2009, vol. 74, pp. 995-1006.
Nodwell, M.; Riffell, J. L.; Roberge, M.; Andersen, R. J.; Synthesis of Antimitotic Analogs of the Microtubule Stabilizing Sponge Alkaloid Ceratamine A; Organic Letters 2008, vol. 10, pp. 1051-1054.
Waly, M. A., Synthesis of the Imidazo[4,5-d]Azepine Ring System, Journal für praktische Chemie 1994, vol. 336, pp. 86-88.
Collison, C. G.; Chen, J.; Walvoord, R.; The First Total Synthesis of the Proposed Structure of Montiporyne E; Synthesis 2006, pp. 2319-2322.
Lewin, A. H.; Szewczyk, J.; Wilson, J. W.; Carroll, F. I.; Galanthamine analogs: 6H-benzofuro[3a,3,2,-e,f][1]benzazepine and 6H-benzofuro[3a,3,2-e, f][3]benzazepine; Tetrahedron 2005, vol. 61, pp. 7144-7152.
Meshram, H. M.; Reddy, P. N.; Sadashiv, K.; Yadav, J. S.; Amberlyst-15-promoted efficient 2-halogenation of 1,3-keto-esters and cyclic ketones using N-halosuccinimides; Tetrahedron Letters 2005, vol. 46, pp. 623-626.
Yang, J. W.; Hechavarria Fonseca, M. T.; List, B.; A Metal-Free Transfer Hydrogenation: Organocatalytic Conjugate Reduction of a,b-Unsaturated Aldehydes; Angewandte Chemie, Int. Ed. 2004, vol. 43, pp. 6660-6662.
Garden, S. J.; Guimaraes, C. R. W.; Correa, M. B.; De Oliveira, C. A. F.; Pinto, A. C.; De Alencastro, R. B.; Synthetic and Theoretical Studies on the Reduction of Electron Withdrawing Group Conjugated Olefins Using the Hantzsch 1,4-Dihydropyridine Ester; Journal of Organic Chemistry. 2003, vol. 68, pp. 8815-8822.
Zolfigol, M. A.; Safaiee, M.; Synthesis of 1,4-Dihydropyridines under Solvent-free Conditions; Synlett 2004, vol. 5, pp. 827-828.

(Continued)

*Primary Examiner* — Bruck Kifle
(74) *Attorney, Agent, or Firm* — Dinsmore & Shohl LLP

(57) ABSTRACT

Methods are provided for preparing compounds of the general formula (I)

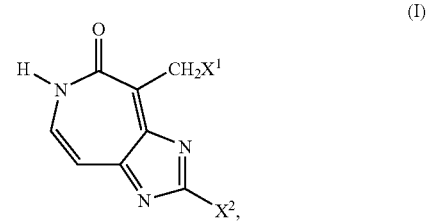

(I)

wherein $X^1$ is an aryl hydrocarbon group optionally substituted with one or more groups independently selected from —R, —NH$_2$, —NHR, —NR$_2$, —OH, —OR, —F, —Cl, —Br, —I, —CF$_3$, —C(=O)OH, —C(=O)OR, —C(=O)NH$_2$, —C(=O)NHR, and —C(=O)NR$_2$; $X^2$ is —H, —R, —NHR, —NR$_2$, —OR, —F, —Cl, —Br, or —I; and R is $C_1$ to $C_{10}$ hydrocarbyl. The methods comprise a double-dehydrogenation reaction step in which a functionalized aminohydroazepinone skeleton comprising an aminoimidazole ring is reacted with 2-iodoxybenzene to form the imidazo[4,5-d]azepine ring system present in formula (I). Example methods comprising the double-dehydrogenation reaction step are provided as efficient synthetic routes to ceratamine A, ceratamine B, and the des-methyl analogs thereof.

20 Claims, No Drawings

OTHER PUBLICATIONS

Legters, J.; Thijs, L.; Zwanenburg, B.; A Convenient Syntheses of Optically Active IH-Aziridine-2-Carboxylic Acids (Esters); Tetrahedron Letters. 1989, vol. 30, pp. 4881-4884.

Guo, Z. X.; Cammidge, A. N.; Horwell, D. C.; A Convenient and Versatile Method for the Synthesis of Protected Guanjdines; Synthesis Communications 2000, vol. 30, pp. 2933-2943.

Nicolaou, K. C.; Montagnon, T.; Baran, P. S.; Modulation of the Reactivity Profile of IBX by Ligand Complexation: Ambient Temperature Dehydrogenation of Aldehydes and Ketones to,-Unsaturated Carbonyl Compounds; Angewandte Chemie, Int. Ed. 2002, vol. 41, pp. 993-996.

Nicolaou, K. C.; Mathison, C. J. N.; Montagnon, T.; New Reactions of IBX: Oxidation of Nitrogen and Sulfur-Containing Substrates to Afford Useful Synthetic Intermediates; Angewandte Chemie, Int. Ed. 2003, vol. 42, pp. 4077-4082.

Nicolaou, K. C.; Mathison, C. J. N.; Synthesis of Imides, N-Acyl Vinylogous Carbamates and Ureas, and Nitriles by Oxidation of Amides and Amines with Dess—Martin Periodinane; Angewandte Chemie, Int. Ed. 2005, vol. 44, pp. 5992-5997.

Roberts, R. M.; Vogt, P. J.; Ortho Esters, Imidic Esters and Amidines. VII. N-Alkylformanilides from Alkyl Orthoformates and Primary Aromatic Amines; Rearrangement of Alkyl N-Arylformimidates; Journal of the American Chemical Society. 1956, vol. 78, pp. 4778-4782.

Crochet, R. A., Jr.; Blanton, C. D., Jr.; N-Monoalkylation of Primary Aromatic and Heteroaromatic Amines with Trialkyl Orthocarobxylates and Sodium Borohydride; Syntheis 1974, pp. 55-56.

SYNTHETIC METHOD FOR CERATAMINE A AND B AND ANALOGS THEREOF

CROSS-REFERENCE TO RELATED APPLICATIONS

This application claims the benefit of priority under 35 U.S.C. §119(e) from U.S. Provisional Application Ser. No. 61/159,108, filed Mar. 11, 2009, the entire disclosure of which is hereby incorporated by reference.

FIELD OF THE INVENTION

The present invention relates general to methods of organic synthesis and, more particularly, to methods for preparing ceratamine A, ceratamine B, and analogs thereof.

BACKGROUND OF THE INVENTION

The marine natural products ceratamine A and B, isolated from the New Guinean sponge *Pseudoceratina* sp., have been shown to possess antimitotic activity in a cell-based assay. These unusual heterocyclic compounds and their analogs join a large family of marine natural products that exhibit antimitotic activity, such as by arresting cells in mitosis, or by stimulating microtubule polymerization in the absence of normally associated proteins. The ceratamines do not compete with taxol for binding to β-tubulin, whereas taxol, the epothilones, discodermolide, and the eleuthesides bind to a common site, which itself is distinct from the binding site of the *Vinca* alkaloids. Thus, the ceratamines may exhibit a unique spectrum of antitumor activity.

The ceratamines possess an unusual imidazo[4,5-d] azepine ring system that presumably results from the oxidative coupling of a brominated tyrosine and a histidine. Dibromotyrosine-containing natural products are typical of sponges of the order Verongida, which includes the genus *Pseudoceratina*, and many such metabolites possess interesting biological activity.

U.S. Patent Application Publication 2008/0255090 by Andersen et al. discloses various possible synthetic routes to ceratamines A and B and analogs thereof. The key steps of these synthetic routes rely on a ring-closing olefin metathesis reaction to form the necessary ring structure. However, none of the synthetic routes proposed by Andersen et al. provide a direct pathway from a functionalized aminohydroazepinone skeleton comprising an aminoimidazole ring to the imidazo [4,5-d]azepine ring system of the ceratamines and their analogs.

As a result of the low natural-abundance of ceratamines, typical for sponge-derived secondary metabolites, any preclinical studies of the ceratamines will rely on the availability of usable and significant quantities of synthetic material. Therefore, there exists a strong need for direct and efficient synthetic routes to ceratamines and their analogs in appreciable yields.

SUMMARY OF THE INVENTION

Embodiments disclosed herein are directed to methods for preparing a compound of the general formula (I)

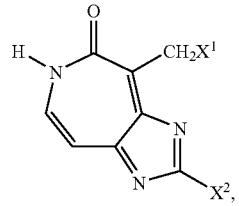

(I)

wherein $X^1$ is an aryl hydrocarbon group optionally substituted with one or more groups independently selected from —R, —NH$_2$, —NHR, —NR$_2$, —OH, —OR, —F, —Cl, —Br, —I, —CF$_3$, —C(=O)OH, —C(=O)OR, —C(=O) NH$_2$, —C(=O)NHR, and —C(=O)NR$_2$; $X^2$ is —H, —R, —NH$_2$, —NHR, —NR$_2$, —OR, —F, —Cl, —Br, or —I; and R is C$_1$ to C$_{10}$ hydrocarbyl. Molecules of formula (I) define a class of molecules generally referred to herein as "ceratamine analogs." In the methods for preparing compound of formula (I), a compound of the general formula (II)

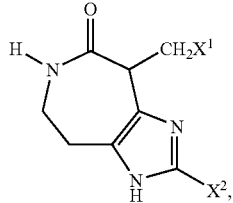

(II)

or a salt thereof, with $X^1$, $X^2$, and R defined as in formula (I), may be reacted with 2-iodoxybenzoic acid in an organic solvent to effect a double dehydrogenation of the lactam ring.

Further embodiments are directed to a method for preparing compounds of the formula (IIIB)

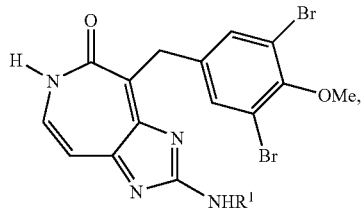

(IIIB)

wherein group $R^1$ is hydrogen or methyl. Compounds of formula (IIIB) may be prepared by dehydrogenating a compound of formula (IV)

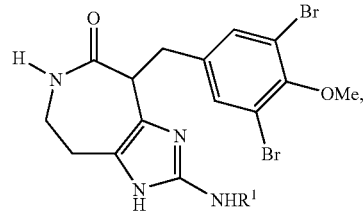

(IV)

with $R^1$ defined as in formula (IIIB), or a suitable salt thereof, with 2-iodoxybenzoic acid in an organic solvent. The method may further comprise preparing the compound of formula (IV) and may comprise additionally preparing one or more precursors to the compound of formula (IV).

Still further embodiments are directed to a method for preparing compounds of formula (IIIA)

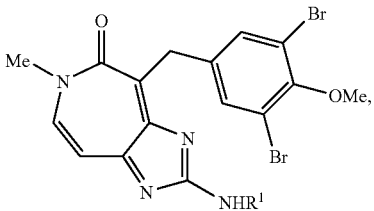

wherein $R^1$ is hydrogen or methyl. Compounds of formula (IIIB) may be prepared by first dehydrogenating a compound of formula (IV)

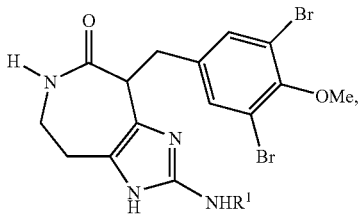

or a suitable salt thereof, with 2-iodoxybenzoic acid in an organic solvent to form a compound of formula (IIIB)

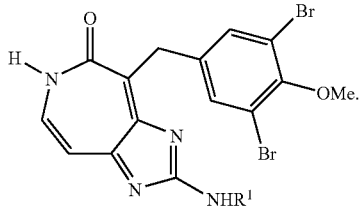

Subsequently, the lactam nitrogen of compound of formula (IIIB) may be methylated to form the compound of formula (IIIA).

These and other features, aspects, and advantages of the present invention will become better understood with reference to the following detailed description and appended claims.

DETAILED DESCRIPTION

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The term "independently selected from," as used in the specification and appended claims, means that the selection for one variable from a list is made independently from the selection for any other variable from the same list. For example, the phrase "$X^1$, $X^2$, and $X^3$ are independently selected from A, B, and C" is intended to encompass the scenarios where $X^1$, $X^2$, and $X^3$ are all identical, where $X^1$, $X^2$, and $X^3$ are all different, and where any two of $X^1$, $X^2$, and $X^3$ are identical to each other but different from the third.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. One of ordinary skill in the art will understand that any numerical values inherently contain certain errors attributable to the measurement techniques used to ascertain the values.

It will be appreciated by those skilled in the art that many compounds described herein naturally may exist as mixtures of two or more tautomeric forms. Unless otherwise indicated, the depictions of molecules herein are intended to encompass all equivalent tautomeric forms of the depicted molecules, without any preference to a particular tautomeric form that is specifically shown.

Embodiments disclosed herein are directed to methods for preparing compounds of the general formula (I)

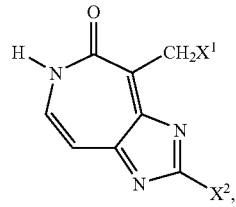

wherein $X^1$ is an aryl hydrocarbon group optionally substituted with one or more groups independently selected from —R, —NH$_2$, —NHR, —NR$_2$, —OH, —OR, —F, —Cl, —Br, —I, —CF$_3$, —C(=O)OH, —C(=O)OR, —C(=O)NH$_2$, —C(=O)NHR, and —C(=O)NR$_2$; $X^2$ is —H, —R, —NH$_2$, —NHR, —NR$_2$, —OR, —F, —Cl, —Br, or —I; and R is $C_1$ to $C_{10}$ hydrocarbyl, alternatively $C_1$ to $C_6$ hydrocarbyl, alternatively $C_1$ to $C_3$ hydrocarbyl. Molecules of formula (I) define a class of molecules generally referred to herein as "ceratamine analogs." As used herein, the term "hydrocarbyl" encompasses linear groups, branched groups, or cyclic groups, each consisting of carbon and hydrogen atoms, wherein any two neighboring carbon atoms may be joined by a single bond or a double bond. The term "$C_1$ to $C_{10}$ hydrocarbyl" refers to hydrocarbyl groups having from 1 to 10 carbon atoms. Thus, example groups $R^1$ include, but are not limited to, methyl, ethyl, vinyl, propyl, 1-methylethyl(isopropyl), butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, cyclopentyl, cyclohexyl, cyclohexenyl, phenyl, benzyl, tolyl, and naphthyl.

The aryl hydrocarbon groups represented by $X^1$ in formula (I) are aromatic hydrocarbon ring structures that may comprise one or more rings, each having from 4 to 10 carbon atoms, alternatively 6 to 10 carbon atoms, alternatively 5 or 6 carbon atoms, alternatively 6 carbon atoms. Example aryl structures include, but are not limited to, phenyl, naphthyl, phenanthrenyl, and anthracenyl. The rings may be unsubstituted, such that each carbon atom in the aromatic ring structure is bonded only to adjoining carbons in the ring structure and hydrogen. Alternatively, one or more individual carbon atoms in the aromatic ring structure may be substituted with a group selected from the group consisting of —R, —NH$_2$, —NHR, —NR$_2$, —OH, —OR, —F, —Cl, —Br, —I, —CF$_3$, —C(=O)OH, —C(=O)OR, —C(=O)NH$_2$, —C(=O)NHR, and —C(=O)NR$_2$, with R defined as above. In example embodiments, group $X^1$ may be a phenyl group of the formula:

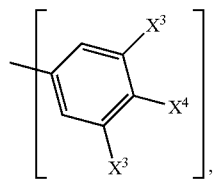

wherein each $X^3$ is independently —H, —F, —Cl, —Br, or —I, and $X^4$ is —H, —CF$_3$, or —OR. In specific example embodiments, each $X^3$ is independently —Cl or —Br or both groups $X^3$ are —Br. In further example embodiments, group $X^4$ is —H, —OMe, or —OEt, where "Me" represents a methyl group and "Et" represents an ethyl group. In yet another example embodiment, each $X^3$ and $X^4$ are H, such that $X^1$ would represent an unsubstituted phenyl group.

Group $X^2$ of formula (I) may be selected from the group consisting of —H, —R, —NHR, —NR$_2$, —OR, —F, —Cl, —Br, or —I, with R defined as above. In example embodiments, $X^2$ is selected from —NH$_2$, —NHR, or —NR$_2$. In more specific example embodiments, $X^2$ is —NH$_2$ or —NHMe.

In example methods for preparing compound of formula (I), a compound of the general formula (II)

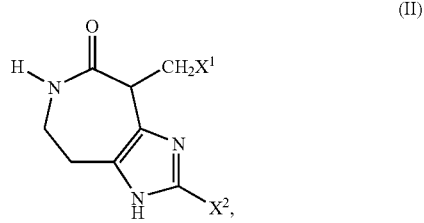

or a salt thereof, with $X^1$, $X^2$, and R defined as in formula (I), may be reacted with 2-iodoxybenzoic acid in an organic solvent to effect a double dehydrogenation of the lactam ring. In non-limiting embodiments, suitable salts of the compound of formula (IV) may include salts having a pK$_a$, less than the pK$_a$ of a protonated imidazole ring on the compound of formula (IV). Specific examples of suitable salts include, but are not limited to, trifluoroacetate salts, hydrochloride salts, and hydrobromide salts. The 2-iodoxybenzoic acid, also known as o-iodoxybenzoic acid or, as referred to hereinafter "IBX," is an iodine(V) reagent having the formula

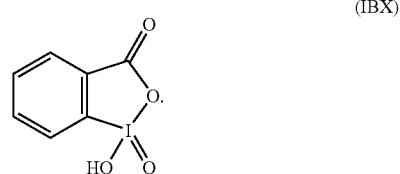

Example organic solvents suitable for the double dehydrogenation reaction include, but are not limited to, dimethylsulfoxide (DMSO), and mixtures of DMSO and a second solvent such as, for example, pyridine. Further details of the double dehydrogenation reaction are illustrated below through specific example embodiments and working Examples, without intent to limit the scope of the present invention to only the compounds described in the example embodiments and working Examples.

In example embodiments, the above method is illustrated with respect to a method for preparing compounds of the formula (IIIB)

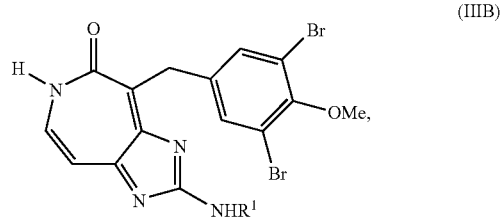

wherein group $R^1$ is hydrogen or methyl. A molecule of formula (IIIB), wherein $R^1$ is methyl, is known also as ceratamine B. A molecule of formula (IIIB), wherein $R^1$ is hydrogen, is known also as the des-methyl analog of ceratamine B. Molecules of formula (IIIB) may be prepared by dehydrogenating a compound of formula (IV)

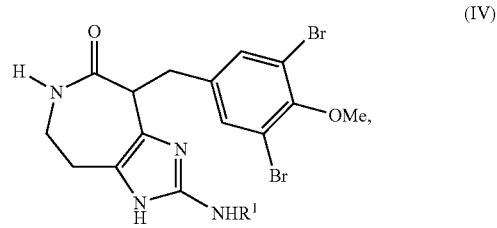

with $R^1$ defined as in formula (IIIB), or a suitable salt thereof, with IBX in an organic solvent. In non-limiting embodiments, suitable salts of the compound of formula (IV) may include salts having a pK$_a$, less than the pK$_a$ of a protonated imidazole ring on the compound of formula (IV). Specific examples of suitable salts include, but are not limited to, trifluoroacetate salts, hydrochloride salts, and hydrobromide salts. In specific examples, the organic solvent may comprise DMSO of mixtures of DMSO with a second solvent such as, for example, pyridine.

In some embodiments, the dehydrogenation of the compound of formula (IV) may comprise two steps. In a first step, the 2-iodoxybenzoic acid may be added to a reaction mixture comprising the compound of formula (IV) and the organic solvent. A reaction may be allowed to progress for a sufficient amount of time, for example, about 1 hour, to drive the dehydrogenation substantially to completion. In a second step, a quenching mixture may be added to the reaction mixture. Without intent to be limited by theory, it is believed that quenching the dehydrogenation reaction may prevent additional dehydrogenations from occurring at other parts of the molecule. Examples of suitable quenching mixtures include a reducing agent and a base. In an example embodiment, the quenching mixture may comprise an aqueous mixture of saturated sodium thiosulfate as the reducing agent and saturated sodium bicarbonate as the base. It will be understood that the selection of the reducing agent and the base are not critical and that many additional possibilities will be apparent to the person of ordinary skill in the art.

The specific double dehydrogenation reaction afforded by the reaction of molecules of formula (IV) in IBX is remarkable in light of the large number of potentially oxidizable sites in molecules of formula (IV). Without intent to be limited by theory, it is suggested that one of several mechanistic pathways are possible. The mechanistic pathways may include an oxidation at the benzylic position followed by elimination, by oxidation at the carbon α to the carbonyl group, or by oxidation of the imidazole ring. In any case, in specific examples, elimination and tautomerization were found to occur during the formation of a des-methyl ceratamine B, as evident in a $^1$H NMR spectrum showing downfield shifts of the benzylic carbons that change from diastereotopic multiplets in molecules of formula (IV) to apparent triplets in molecules of formula (IIIB).

In example embodiments, a compound of the formula (IIIB), in which $R^1$ is methyl, may be prepared by first methylating a compound of formula (XI)

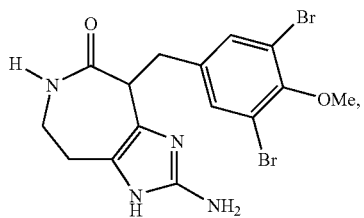

(XI)

to form a compound of formula (IV) with $R^1$ as methyl. Thereafter, the compound of formula (IV) may be dehydrogenated in IBX. As part of a preparation of a compound of formula (IIIB) with $R^1$ as methyl from a compound of formula (IV) with $R^1$ as hydrogen (i.e., a compound of formula (XI)), methylation of the amino group of the compound of formula (IV) with $R^1$ as hydrogen preferably is accomplished before the dehydrogenation step. Generally, methylation of the amino group in compounds of the formula (IIIB) with $R^1$ as hydrogen is impractical using reductive alkylation conditions, owing substantially to the sensitivity toward reduction of fully oxidized, heterocyclic ring systems such as those present in compounds of formula (IIIB).

The methylation may be accomplished by reacting the compound of formula (XI), or a suitable salt thereof, with a molar equivalent amount of triethyl orthoformate (HC(OEt)$_2$) to form a methylation mixture in an appropriate solvent, for example, in ethanol. In non-limiting embodiments, suitable salts of the compound of formula (X$^1$) may include salts having a p$K_a$, less than the p$K_a$ of a protonated imidazole ring on the compound of formula (XI). Specific examples of suitable salts include, but are not limited to, trifluoroacetate salts, hydrochloride salts, and hydrobromide salts. The methylation mixture may be allowed to react for a suitable time, for example about 4 hours, at an elevated temperature, for example about 80° C. Thereupon, a reducing agent such as, for example, sodium borohydride, may be added to the methylation mixture. After the reducing agent is added, the reaction may be cooled, for example to the range from about 0° C. to about 40° C., and allowed a suitable time to complete, for example about 1 hour. Without intent to be limited by theory, it is believed that the triethyl orthoformate may cause formation of an ethyl formimidate derivative of the compound of formula (XI) in the methylation mixture. The addition of the reducing agent then may reduce the ethyl formimidate derivative to the methylated compound of formula (IV) with $R^1$ as methyl.

In further example embodiments of preparing compounds of formula (IIIB), the compound of formula (XI) may be prepared by first annulating a 2-aminoimidazole ring onto a compound of formula (IX)

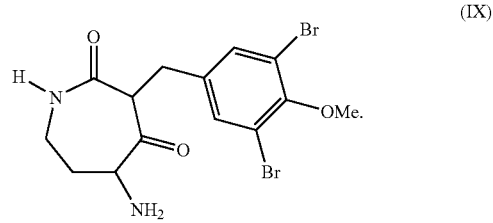

(IX)

The annulation may be accomplished by first introducing a suitably protected amidine group onto the amino group of the compound of formula (IX). One non-limiting example of a suitable protecting group is Boc, a tert-butyl carbamate (—C(=O)OC(CH$_3$)$_3$). In a specific embodiment, the compound of formula (IX) may be reacted with a bis-Boc-protected S-methylisothiourea in an amine base such as triethylamine

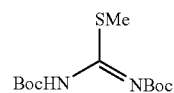

to form a compound of formula (X)

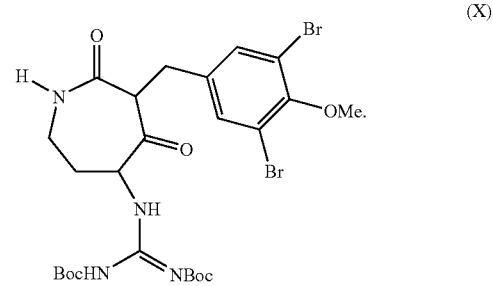

(X)

Thereupon, the bis-Boc-protected compound of formula (X) may be deprotected during a concomitant condensation reaction that results in a ring closing to form the compound of formula (XI).

The reaction to attach the protected amidine group to the compound of formula (IX) may be accomplished in a suitable reaction vessel under example conditions of low temperature such as 0° C. in a cooled protection solution for a sufficient amount of time, for example about 1 hour. The reaction may be facilitated through the addition of a thiophilic metal such as, for example, Hg, Ag, Zn, Pd, Cd, Pt, or Au, to the reaction vessel in the form of a thiophilic metal salt, for example, as $HgCl_2$ or AgCl. The reaction may be further facilitated through the addition of an amine base such as, for example, triethylamine. The reaction may also be favorable in organic solvents including, such as, for example, methanol.

The deprotection and condensation reaction to form the compound of formula (XI) from the compound of formula (X) may be acid-promoted, such as through a deprotecting acid. In a specific example, the compound of formula (X) may be converted to the compound of formula (XI) by adding trifluoroacetic acid to the reaction vessel, for example, at room temperature, for a suitable time, for example about 1 hour. In this specific example, a trifluoroacetate salt of the compound of formula (XI) is formed. Nevertheless, it will be understood that other deprotecting acids such as, for example, hydrochloric acid or hydrobromic acid, may be used to accomplish the deprotection and condensation and that other salts such as, for example, hydrochloride salts or hydrobromide salts, would result from the use of such deprotecting acids. Under typical conditions, the two-step preparation of the compound of formula (XI) from the compound of formula (X) may result in substantially quantitative yields.

In still further example embodiments of a method for preparing compounds of formula (IIIB), the method may further comprise preparing the amine compound of formula (IX). The compound of formula (IX) may be prepared via hydrogenolysis of an azide compound of formula (VIII)

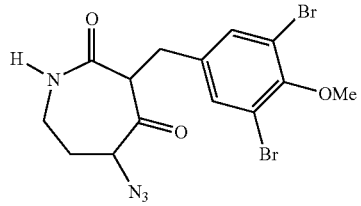

(VIII)

to form the compound of formula (IX). The hydrogenolysis may be conducted by exposing the compound of formula (VIII) to hydrogen at a suitable pressure and temperature, for a suitable amount of time. The hydrogenolysis may be facilitated by employing a supported noble-metal catalyst. The supported noble-metal catalyst may comprise a noble metal such as, for example, platinum or palladium, supported on an alkaline earth metal salt. In specific example embodiments, the hydrogenolysis may be conducted using a palladium catalyst adsorbed onto $BaSO_4$. With such a catalyst, the compound of formula (VIII) may be exposed to about 1 atm of hydrogen in, for example, a hydrogenation solvent such as methanol, at about room temperature for about 2 hours to yield the compound of formula (IX). In all instances, the selection of pressure, temperature, time, and catalyst must take include consideration of the need to avoid appreciable hydrogenolysis of the aryl bromides from the compound of formula (VIII). Although metal-catalyzed hydrogenolysis of the azide may not represent the most readily apparent and straightforward pathway because of the potentially labile aryl bromides, use of the reductant $Ph_3P$ in an alternate embodiment is not preferred, because the adjacent ketone may intercept the intermediate phosphinimine to form a stable oxazaphospholidine.

In still further example embodiments of a method for preparing compounds of formula (IIIB), the method may further comprise preparing the compound of formula (VIII). The compound of formula (VIII) may be prepared in a multi-step synthetic route from a compound of formula (V)

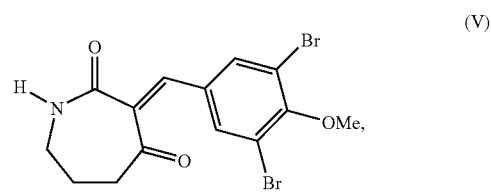

(V)

wherein the compound of formula (V) first is reacted with a brominating agent in a suitable solvent. A non-limiting example of a suitable brominating agent may include N-bromosuccinimide or bromine ($Br_2$), for which a suitable solvent may include, for example, ethyl acetate or acetic acid. The bromination may be facilitated by adding catalysts such as Amberlyst-15 and brominating at about room temperature for about 24 hours. The bromination of the compound of formula (V) thus results in a compound of formula (VI)

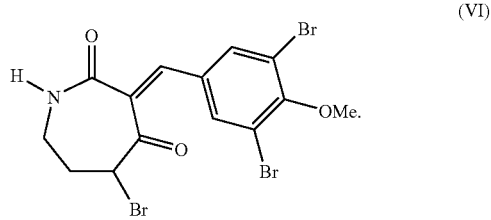

(VI)

The synthetic route may further comprise conjugate reduction of a double bond in the compound of formula (VI) by reaction with a suitable conjugate reduction agent in a suitable solvent system. An example suitable conjugate reduction agent in this regard is Hantzsch ester, the Hantzsch ester having the structure

(Hantzsch ester)

When Hantzsch ester is used as the conjugate reduction agent, a non-limiting example suitable solvent system may comprise ethanol and benzene. The conjugate reduction of the compound of formula (VI) may result in a compound of formula (VII)

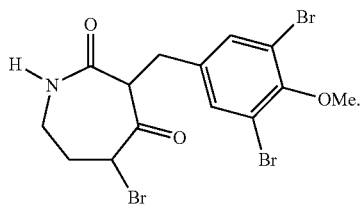

(VII)

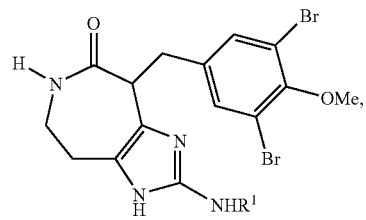

(IV)

in high yield (25° C., 12 hours) without over-reduction of the α-bromide. Thereupon, the compound of formula (VII), may be reacted with an azide source in a polar aprotic solvent to form the compound of formula (VIII) in substantially quantitative yield. In a non-limiting specific example, sodium azide may be used as the azide source. Non-limiting examples of aprotic solvents include dimethylsulfoxide, dimethylformamide, acetonitrile, and acetone. In a specific example embodiment, the azide source may comprise sodium azide and the aprotic solvent may comprise DMSO.

In still further example embodiments of a method for preparing compounds of formula (IIIB), the method further comprises preparing the compound of formula (V). The compound of formula (V) may be prepared by first reacting 4-ethoxy-6,7-dihydro-1H-azepin-2(5H)-one with hydrochloric acid in acetone to form azepane-2,4-dione. The 4-ethoxy-6,7-dihydro-1H-azepin-2(5H)-one may be prepared from 3-ethoxy-2-cyclohexenone by Beckmann rearrangement. Then, the azepane-2,4-dione may be reacted with 3,5-dibromo-4-methoxybenzaldehyde (3,5-dibromoanisaldehyde) in a suitable solvent system at a suitable temperature for a suitable amount of time. For example, the reaction may be conducted at room temperature for about 1 hour. A non-limiting example of a suitable solvent system may include dichloromethane, acetic acid, piperidine, and mixtures thereof, to form the compound of formula (V).

The above example embodiments of a method for preparing compounds of formula (IIIB) may be applied further to a method for preparing compounds of formula (IIIA)

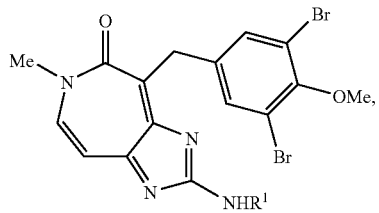

(IIIA)

wherein $R^1$ is hydrogen or methyl. A molecule of formula (IIIA), wherein $R^1$ is methyl, is known also as ceratamine A. A molecule of formula (IIIA), wherein $R^1$ is hydrogen, is known also as the des-methyl analog of ceratamine A. Molecules of formula (IIIA) may be prepared by first dehydrogenating a compound of formula (IV)

or a salt thereof, with IBX in an organic solvent to form a compound of formula (IIIB)

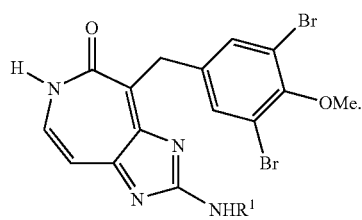

(IIIB)

In non-limiting embodiments, suitable salts of the compound of formula (IV) may include salts having a $pK_a$ less than the $pK_a$ of a protonated imidazole ring on the compound of formula (IV). Specific examples of suitable salts include, but are not limited to, trifluoroacetate salts, hydrochloride salts, and hydrobromide salts. In example embodiments, the organic solvent may be selected from the group consisting of dimethylsulfoxide and mixtures of dimethylsulfoxide and a second solvent such as, for example, pyridine.

Thereupon, a lactam nitrogen of the compound of formula (IIIB) may be methylated to form the compound of formula (IIIA). The methylation of the lactam nitrogen may be accomplished by any suitable means known for replacing a lactam hydrogen with a lactam methyl group. In example embodiments, the methylation may be accomplished from a solution containing the compound of formula (IIIB) in an appropriate solvent system. A strong base and a methylation agent may be added to the solution. In example embodiments, the strong base may be selected from an amide base or a hydride base. An example appropriate solvent system may comprise dimethylformamide (DMF), tetrahydrofuran (THF), or mixtures thereof, for example, a 1:1 molar-ratio mixture of DMF and THF. Examples of strong bases for use in the methylation may include bis(organosilyl)amide salts such as, for example, sodium bis(trimethylsilyl)amide. Examples of methylation agents include methyl halides such as, for example, iodomethane. Further examples of methylation agents include dimethyl sulfate and methyl triflate. In a specific example embodiment, iodomethane may be used as the methylation agent, sodium bis(trimethylsilyl amide may be used as the strong base, and a mixture of DMF and THF may be used as the solvent system. In example embodiments, the base may be added dropwise to the solution while the solution is held at a low temperature such as, for example, about 0° C. In further example embodiments, the solution may be cooled further, for example to about −78° C., when the methylation agent is added. In still further example embodiments, the methylation reaction may be quenched, for example, by adding water.

EXAMPLES

The present invention will be better understood by reference to the following examples, which are offered by way of illustration and which one of skill in the art will recognize are not meant to be limiting.

General Methods: $^1$H (500 MHz or 400 MHz) and $^{13}$C (125 MHz or 100 MHz) NMR spectra were recorded on a Bruker DRX-500 or Bruker DPX-400 spectrometer in CDCl$_3$ using CHCl$_3$ ($^1$H δ 7.26) and CDCl$_3$ ($^{13}$C δ 77.0) or DMSO-d$_6$ using DMSO (1H δ 2.49) and DMSO-d$_6$ ($^{13}$C δ 39.51) as internal standards. High resolution mass spectra were recorded on a Bruker MicrOTOF ESI spectrometer provided by OBIC. All reactions were conducted in either oven-dried (120° C.) glassware or flame-dried glassware, under an N$_2$ atmosphere when necessary. Tetrahydrofuran (THF) was distilled from benzophenone ketyl. Triethylamine and CH$_2$Cl$_2$ were distilled from calcium hydride prior to use. N-bromosuccinamide was crystallized from H$_2$O prior to use. All other chemicals were used as received.

Example 1

4-Ethoxy-6,7-dihydro-1H-azepin-2(5H)-one

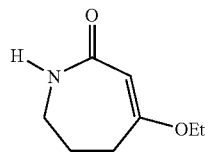

A solution of methanesulfonyl chloride (2.1 mL, 26.5 mmol) in dichloromethane (27 mL) was added dropwise via cannula to a solution of oxime (2.74 g, 17.7 mmol) and triethylamine (3.7 mL, 26.5 mmol) in CH$_2$Cl$_2$ (40 mL) at 0° C. Upon completion of addition, the cloudy solution was diluted with CH$_2$Cl$_2$ (50 mL) and poured onto ice-cold water (100 mL). The mixture was extracted with dichloromethane (3×50 mL), and the combined organic extracts were dried (Na$_2$SO$_4$) and concentrated in vacuo to afford a yellow oil, which was diluted with benzene (15 mL) and loaded immediately onto a column of neutral alumina. The oil was left on the column for 12 hours and was eluted sequentially with hexane (200 mL), benzene (150 mL), and methanol (200 mL). The product was eluted from the column with the methanol fraction and the methanol was removed in vacuo. The resulting yellow residue was diluted with dichloromethane (50 mL) and was washed with 5% aqueous sodium bicarbonate (50 mL), and the mixture was extracted with CH$_2$Cl$_2$ (3×30 mL). The combined organic extracts were dried (Na$_2$SO$_4$), filtered, and concentrated in vacuo to afford the crude product 4-ethoxy-6,7-dihydro-1H-azepin-2(5H)-one (2.4 g, 87%) as a yellow solid, which was used without further purification: $^1$H NMR (400 MHz, CDCl$_3$) d 6.52 (br s, NH), 5.07 (s, 1H), 3.80 (q, J=7.0 Hz, 2H), 3.23 (m, 2H), 2.49 (t, J=7.0 Hz, 2H), 1.96 (m, 2H), 1.32 (t, J=7.0 Hz, 3H); $^{13}$C NMR (100 MHz, CDCl$_3$) d 172.3, 167.9, 96.6, 63.5, 41.1, 32.7, 27.0, 14.3; IR (neat) nmax 3260, 2986, 2975, 2931, 1675, 1587, 1460, 1428, 1352, 1244, 1163, 1119 cm$^{-1}$; HRMS (ESI) m/z calcd for C$_8$H$_{13}$NO$_2$Na: 178.0844. found: 178.0840.

Example 2

Azepane-2,4-dione

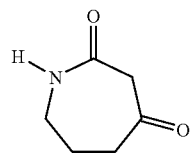

A solution of 10% aqueous HCl (17 mL) was added to an acetone solution (70 mL) of the 4-ethoxy-6,7-dihydro-1H-azepin-2(5H)-one (2.5 g, 16 mmol) from Example 1 at 25° C. The reaction mixture was stirred for 12 hours. The acetone was removed in vacuo, and the resulting mixture was extracted with CH$_2$Cl$_2$ (10×15 mL). The combined organic extracts were dried (Na$_2$SO$_4$), filtered, and concentrated in vacuo to afforded the crude product as a yellow solid. Purification by flash column chromatography (silica, 10% MeOH/EtOAc) afforded azepane-2,4-dione (2.03 g, 100%) as a white solid: $^1$H NMR (400 MHz, CDCl$_3$) d 7.55 (s, NH), 3.47 (s, 2H), 3.40 (m,), 2.59 (t, J=6.8 Hz, 2H), 1.96 (m, 2H); $^{13}$C NMR (100 MHz, CDCl$_3$) d 202.5, 169.5, 51.9, 43.2, 40.8, 27.6; IR (KBr) nmax 3213, 3105, 2942, 1702, 1671, 1482, 1412, 1348 cm$^{-1}$; HRMS (ESI) m/z calcd for C$_6$H$_9$NO$_2$Na: 150.0525. found: 150.0507.

Example 3

(Z)-3-(3,5-Dibromo-4-methoxybenzylidene) azepane-2,4-dione

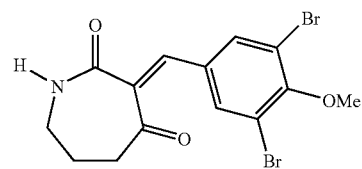

(V)

Dichloromethane (18 mL), the azepane-2,4-dione from Example 2 (4.5 g, 35.8 mmol), 3,5-dibromo-4-methoxybenzaldehyde (9.5 g, 32.6 mmol), and 3-Åmolecular sieves (3.2 g) were added to a 50 mL two-neck round-bottomed flask equipped with a calcium chloride drying tube. Piperidine (0.27 mL, 3.26 mmol) and acetic acid (0.24 mL, 3.26 mmol) were added simultaneously at 25° C. to the vigorously stirred mixture. The reaction mixture was stirred at this temperature for 30 minutes and additional molecular sieves (3.2 g) were added. Stirring was continued for 4 hours during which time heterogeneous reaction mixture solidified. The solid was slurried with CH$_2$Cl$_2$, molecular sieves were removed by filtration, and the filtrate was concentrated in vacuo to afford a crude product of formula (V) as a beige solid (14.4 g, 100%), which was used without further purification: (400 MHz, CDCl$_3$) d 7.85 (s, 2H), 7.64 (s, 1H), 7.07 (m, 1H), 3.90 (s, 3H), 3.45 (m, 2H), 2.81 (t, J=7.1 Hz, 2H), 2.08 (m, 2H); $^{13}$C NMR (100 MHz, CDCl$_3$) d 195.3, 170.9, 156.1, 140.1, 135.2, 60.8, 39.5, 38.1, 26.9; IR (KBr) nmax 3181, 3060, 2939, 1690, 1646, 1591, 1470, 1415, 1256, 1124, 971 cm$^{-1}$; HRMS (ESI) m/z calcd for $C_{14}H_{14}Br_2NO_3$: 401.9335. found: 401.9318.

Example 4

(Z)-3-(3,5-Dibromo-4-methoxybenzylidene)-5-bromoazepane-2,4-dione

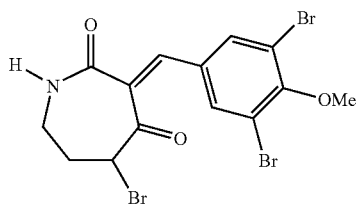

(VI)

Amberlyst®-15 hydrogen form resin (a styrene-divinylbenzene macroreticular resin, registered trademark of Rohm and Haas Co.; 5.2 g) and N-bromosuccinimide (1.4 g, 7.5 mmol) were added to a solution of the product of formula (V) from Example 3 (3.0 g, 6.8 mmol), in ethyl acetate (68 mL), in the dark at 25° C. The reaction mixture was stirred in the dark for 2 days. The mixture was diluted with EtOAc (500 mL), filtered, washed with $H_2O$ (3×50 mL), and was dried ($Na_2SO_4$) and concentrated in vacuo. Purification of the residue by trituration (25° C., $CHCl_3$) afforded a product of formula (VI) (2.2 g, 67%) as a white powder: $^1$H NMR (400 MHz, DMSO) d 8.60 (m, NH), 8.03 (s, 2H), 7.69 (s, 1H), 5.23 (m, 1H), 3.82 (s, 3H), 3.31 (m, 2H), 2.67 (m, 1H), 2.20 (m, 1H); $^{13}$C NMR (100 MHz, DMSO-$d_6$) d 188.2, 167.6, 155.0, 140.5, 135.0, 133.3, 132.2, 117.5, 60.62, 53.4, 38.5, 37.6; IR (KBr) nmax 3198, 3047, 2927, 1704, 1660, 1595, 1471, 1389, 1264, 1123 cm$^{-1}$; HRMS (ESI) m/z calcd for $C_{14}H_{12}Br_3NO_3Na$: 503.8239. found: 503.8243.

Example 5

3-(3,5-Dibromo-4-methoxybenzyl)-5-bromoazepane-2,4-dione

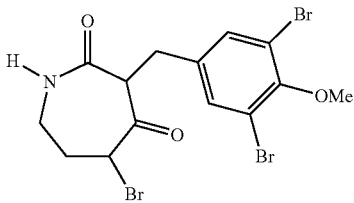

(VII)

Hantzsch ester (0.68 g, 2.7 mmol) was added to a solution of the product of formula (VI) from Example 4 (1.2 g, 2.4 mmol) in benzene (20 mL) and ethanol (20 mL) at 25° C. The reaction mixture was stirred for additional 24 hours at this temperature, during which time it became homogeneous. The solvent was removed in vacuo, and purification of the residue by flash column chromatography (silica, $Et_2O$) afforded a product of formula (VII) (1.1 g, 88%) as a white foam as a mixture of inseparable diastereomers. The major isomer was characterized: $^1$H NMR (500 MHz, $CDCl_3$) d 7.36 (s, 2H), 4.89 (m, 1H), 4.55 (m, 1H), 4.03 (m, 1H), 3.82 (s, 3H), 3.23 (m, 1H), 3.12 (m, 1H), 3.03 (m, 1H), 2.47 (m, 1H), 2.33 (m, 1H); $^{13}$C NMR (125 MHz, $CDCl_3$) d 195.3, 168.9, 152.7, 137.6, 133.5, 117.8, 60.8, 55.1, 53.3, 38.8, 36.8, 30.0; IR (KBr) nmax 3272, 2931, 1719, 1672, 1489 cm$^{-1}$; HRMS (ESI) m/z calcd for $C_{14}H_{14}Br_3NO_3Na$: 505.8396. found: 505.8395.

Example 6

3-(3,5-Dibromo-4-methoxybenzyl)-5-azidoazepane-2,4-dione

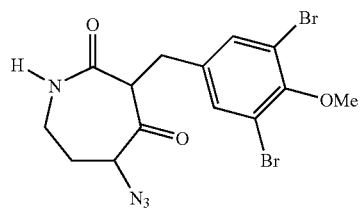

(VIII)

Sodium azide (195 mg, 2.99 mmol) was added to a solution of the product of formula (VII) from Example 5 (480 mg, 0.998 mmol) in DMSO (5 mL) at 25° C. The reaction mixture was stirred for 1 hour at this temperature and was cooled to 0° C. The reaction was quenched by the addition of cold water (5 mL) and cold ether (5 mL), and was extracted with ether (5×5 mL). The combined organic extracts were dried ($Na_2SO_4$) and concentrated in vacuo to afford a crude product of formula (VIII) as a mixture of diastereomers (445 mg, 0.998 mmol, 100%), which were used without further purification. The major isomer was characterized: $^1$H NMR (500 MHz, $CDCl_3$) δ 7.33 (s, 2H), 7.20 (m, NH), 4.11 (dd, J=12.0, 6.5 Hz, 1H), 4.03 (t, J=6.7 Hz, 1H), 3.82 (s, 3H), 3.75 (m, 1H), 3.39 (m, 1H), 3.13 (m, 2H), 2.37 (m, 1H), 1.92 (m, 1H); $^{13}$C NMR (125.7 MHz, $CDCl_3$) δ 199.1, 167.5, 152.8, 137.8, 133.4, 118.1, 69.6, 60.7, 56.7, 39.5, 36.5, 30.2; IR (neat) nmax 3314, 2929, 2104, 1718, 1675, 1473 cm$^{-1}$; HRMS (ESI) m/z calcd for $C_{14}H_{14}Br_2N_4O_3Na$: 466.9325. found 466.9355.

Example 7

3-(3,5-Dibromo-4-methoxybenzyl)-5-($N^2,N^3$-bis(tertbutoxycarbonyl)guanidino)azepane-2,4-dione

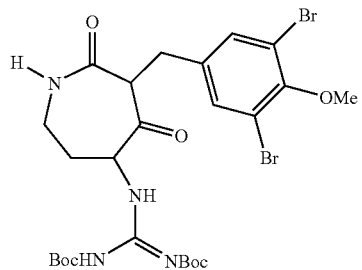

(X)

Hydrogen gas was bubbled through a solution of the product of formula (VIII) from Example 6 (150.9 mg, 0.338 mmol), concentrated HCl (30 µL, 0.338 mmol), and 5% Pd on BaSO$_4$ (30.2 mg, 20% w/w) in methanol (1.7 mL) for 2 hours. The reaction mixture was filtered through Celite® (diatomaceous earth; registered trademark of Fluka) and washed with a minimal amount of methanol (2 mL). The filtrate was cooled to 0° C. and HgCl$_2$ (110 mg, 0.406 mmol), Et$_3$N (0.470 mL, 3.38 mmol), and 1,3-bis(tert-butoxycarbonyl)-2-methyl-2-thiopseudourea (118 mg, 0.406 mmol) were added sequentially. The reaction mixture was stirred for 1 hour at 0° C., and was filtered and concentrated in vacuo to afford a crude product of the formula (X) as a beige solid. Purification of the crude product by flash chromatography (silica, 40% EtOAc/hexane) afforded a pure compound of the formula (X) (165.3 mg, 74%) as a white foam: $^1$H NMR (500 MHz, CDCl$_3$) δ 11.35 (s, NH), 9.20 (d, J=6.4 Hz, NH), 7.34 (s, 2H), 6.50 (m, NH), 4.99 (m, 1H), 4.12 (m, 1H), 3.85 (s, 3H), 3.34 (m, 1H), 3.24 (dd, J=14.4, 6.4 Hz, 1H), 3.04 (dd, J=14.4, 7.2 Hz, 1H), 2.82 (m, 1H), 1.69 (m, 2H), 1.51 (s, 9H), 1.48 (s, 9H); $^{13}$C NMR (125 MHz, CDCl$_3$) δ 199.5, 167.0, 163.1, 155.0, 152.7, 137.9, 133.4, 118.0, 83.6, 79.6, 62.0, 60.5, 57.1, 38.9, 37.4, 30.2, 28.2, 28.1; IR (neat) nmax 3310, 2978, 2931, 1724, 1676, 1647, 1618, 1474, 1420, 1368, 1152 cm$^{-1}$; HRMS (ESI) m/z calcd for C$_{25}$H$_{35}$Br$_2$N$_4$O$_7$: 661.0867. found: 661.0871.

Example 8

Tetrahydro-des-Methyl Ceratamine B Trifluoroacetic Acid Salt

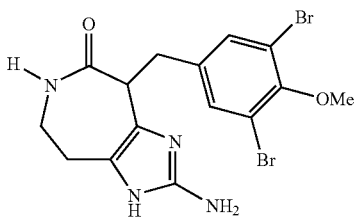

(XI)

Trifluoroacetic acid (2 mL) was added to a solution of the product of formula (X) from Example 7 (165 mg, 0.250 mmol) in dichloromethane (2 mL). The reaction mixture was stirred at 25° C. for 1 hour. The solvent was removed in vacuo, and the resulting yellow oil was crystallized from THF (2 mL) to afford a pure product of the trifluoroacetic acid salt of the compound of formula (XI) (140 mg, 100%) as a white solid: $^1$H NMR (500 MHz, DMSO) δ 12.3 (br s, NH), 12.0 (br s, NH), 7.84 (m, NH), 7.55 (br s, 4H), 3.83 (m, 1H), 3.76 (s, 3H), 3.51 (m, 1H), 3.43 (m, 1H), 3.06 (m, 2H), 2.56 (br s, 2H); $^{13}$C NMR (125 MHz, DMSO) δ 171.4, 151.8, 146.5, 138.2, 133.3, 120.9, 117.0, 116.9, 60.3, 44.1, 37.1, 35.2, 25.4; IR (KBr) nmax 3422, 3184, 2976, 2812, 1685, 1473, 1202, 1136 cm$^{-1}$; HRMS (ESI) m/z calcd for C$_{15}$H$_{17}$Br$_2$N$_4$O$_2$: 442.9713. found: 442.9689.

Example 9 des-Methyl Ceratamine B

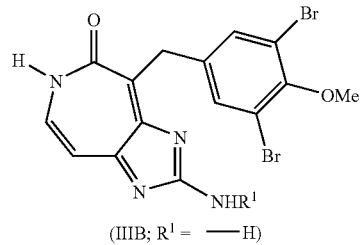

(IIIB; R$^1$ = —H)

2-Iodoxybenzoic acid (IBX) (37.1 mg, 0.133 mmol) was added to a solution of the product of formula (XI) from Example 8 (18.5 mg, 0.033 mmol) and pyridine (13 µL, 0.165 mmol) in DMSO (0.44 mL). The reaction mixture was stirred at 35° C. for 1 hour. The reaction was quenched by the addition of saturated aqueous Na$_2$S$_2$O$_3$ (2 mL), extracted with EtOAc (6×4 mL), and the combined organic extracts were dried (Na$_2$SO$_4$) and concentrated in vacuo to afford a crude product of the formula (XII) as a dark-yellow solid. Purification of the crude product of the formula (IIIb; R$^1$=H) by flash chromatography (C-18 reverse-phase silica, 60% MeOH/H$_2$O) afforded a pure product of the formula (IIIb; R$^1$=H) (12.5 mg, 0.0284 mmol, 86%) as a yellow solid: $^1$H NMR (500 MHz, DMSO) δ 11.45 (d, J=7.6 Hz, NH), 8.32 (br s, NH), 8.20 (br s, NH), 7.55 (s, 2H), 7.18 (app t, J=8.8, 7.6 Hz, 1H), 6.47 (d, J=8.8 Hz, 1H), 4.15 (s, 2H), 3.73 (s, 3H); $^{13}$C NMR (125 MHz, DMSO) δ 176.4, 171.3, 164.5, 162.0, 151.4, 139.9, 138.1, 132.8, 121.1, 116.8, 101.3, 60.3, 34.1; IR (neat) nmax 3336, 1618, 1524, 1472, 1420, 1285 cm$^{-1}$; HRMS (ESI) m/z calcd for C$_{15}$H$_{13}$Br$_2$N$_4$O$_2$: 438.9400. found: 438.9398. Notably, the $^{13}$C NMR chemical shifts at (δ 176.4, 162.0, and 171.3), are representative of a nonaromatic heterocycle, in dramatic contrast to the shifts characteristic of a 2-aminoimidazole (δ 146.5, 117.0, and 120.9) for the compound of formula (XI).

Example 10 des-Methyl Ceratamine A

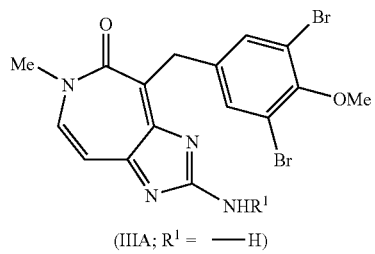

(IIIA; R$^1$ = —H)

Sodium bis(trimethylsilyl)amide (1 M in THF, 31.2 µL, 0.0312 mmol) was added dropwise to a solution of the product of formula (XI) from Example 8 (12.5 mg, 0.0284 mmol) in DMF:THF (1:1, 0.30 mL) at 0° C. The reaction mixture was cooled to −78° C. and iodomethane (3.5 µL, 0.0568 mmol) was added dropwise followed by warming to −10° C. The reaction was quenched by the addition of H$_2$O (2 mL), extracted with EtOAc (6×5 mL), and the combined organic extracts were dried (Na₂SO₄) and concentrated in vacuo to yield crude product of the formula (IIIa; R¹=H). Purification by flash chromatography (C-18 reverse-phase silica, 70% MeOH:H₂O) afforded a pure product of the formula (IIIa; R¹=H) (6.5 mg, 0.0143 mmol, 50%) as a yellow solid. The major tautomer was characterized: $^1$H NMR (500 MHz, DMSO) δ 8.31 (br s, NH), 8.19 (br s, NH), 7.78 (d, J=9.8 Hz, 1H), 7.56 (s, 2H), 6.46 (d, J=9.8 Hz, 1H), 4.20 (s, 2H), 3.72 (s, 3H), 3.56 (s, 3H); $^{13}$C NMR (125 MHz, DMSO) δ 176.6, 170.2, 163.9, 161.3, 151.3, 143.1, 140.1, 132.9, 121.1, 116.7, 100.4, 60.3, 43.8, 35.1; HRMS (ESI) m/z calcd for $C_{16}H_{15}Br_2N_4O_2$: 452.9556. found: 452.9533.

Example 11

Tetrahydro-Ceratamine B

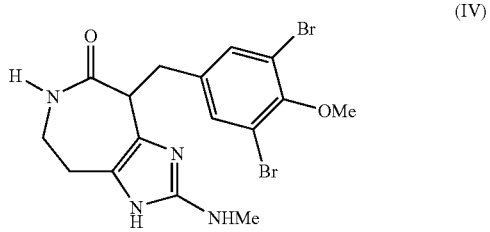

(IV)

The aminoimidazole product of formula (XI) from Example 8 (22.1 mg, 0.0396 mmol) was suspended in triethyl orthoformate (0.4 mL), and the reaction mixture was stirred at 80° C. for 5 hours. The reaction mixture was cooled to 23° C., and the solvent was removed in vacuo. The resulting white solid was dissolved in EtOH (0.20 mL) and cooled to 0° C. Sodium borohydride (3.0 mg, 0.079 mmol) was added in one portion and the reaction mixture was stirred at 40° C. for 1 hour. The mixture was diluted with EtOAc (20 mL), washed with H₂O (3×3 mL), and the combined organic extracts were dried (Na₂SO₄) and concentrated in vacuo to afford a crude product of the formula (IV) (15.0 mg, 0.0327 mmol) as a pale yellow solid, which was used without further purification: HRMS (ESI) m/z calcd for $C_{16}H_{19}Br_2N_4O_2$: 456.9869. found: 456.9849. These data from synthetic ceratamine B are consistent with data reported for natural products.

Example 12

Ceratamine B

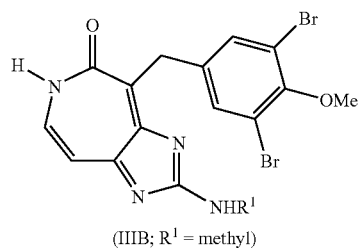

(IIIB; R¹ = methyl)

2-Iodoxybenzoic acid (IBX) (36.6 mg, 0.131 mmol) was added to a solution of the crude product of formula (IV) from Example 11 (15.0 mg, 0.0327 mmol) and pyridine (13 μL, 0.164 mmol) in DMSO (0.44 mL) at 35° C. The reaction mixture was stirred for 1 hour at this temperature, and was quenched by the addition of saturated aqueous Na₂S₂O₄ (2 mL) and saturated NaHCO₃ (1 mL). The reaction mixture was extracted with EtOAc (6×5 mL), the combined organic extracts were dried (Na₂SO₄) and concentrated in vacuo to afford crude ceratamine B (formula (IIIB); R¹=methyl) as an orange solid. Purification by flash chromatography (C-18 reverse-phase silica, 70% MeOH/H₂O) afforded pure ceratamine B (formula (IIIB); R¹=methyl) (12.1 mg, 0.0266 mmol, 81%) as a yellow solid. The major tautomer was characterized: $^1$H NMR (500 MHz, DMSO) δ 11.40 (br d, J=7.9 Hz, NH), 8.67 (br q, J=5.3 Hz, NH), 7.70 (s, 2H), 7.14 (br app t, J=8.5 Hz, 1H), 6.42 (d, J=9.1 Hz, 1H), 4.17 (s, 2H), 3.72 (s, 3H), 3.07 (d, J=5.0 Hz, 3H); $^{13}$C NMR (125 MHz, DMSO) δ 175.4, 170.8, 164.6, 161.2, 151.4, 140.1, 137.9, 133.1, 121.3, 116.6, 101.2, 60.3, 33.9, 29.2; HRMS (ESI) m/z calcd for $C_{16}H_{15}Br_2N_4O_2$: 452.9556. found: 452.9576.

Example 13

Ceratamine A

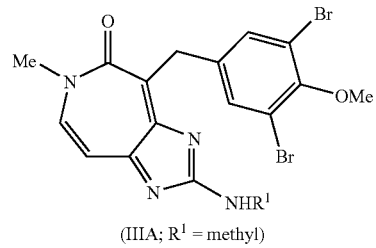

(IIIA; R¹ = methyl)

Sodium bis(trimethylsilyl)amide (1 M in THF, 24 μL, 0.0240 mmol) was added dropwise to a solution of ceratamine B from Example 12 (formula (IIIB); R¹=methyl) (12.1 mg, 0.0266 mmol) in DMF:THF (1:1, 0.27 mL) at 0° C. The reaction mixture was cooled to −78° C. and iodomethane (2.1 μL, 0.0346 mmol) was added dropwise followed by warming to −10° C. The reaction was quenched by the addition H₂O (2 mL), and was extracted with EtOAc (6×5 mL). The combined organic extracts were dried (Na₂SO₄) and concentrated in vacuo to afford crude ceratamine A (formula (IIIA); R¹=methyl). Purification by flash chromatography (C-18 reverse-phase silica, 70% MeOH:H₂O) yielded pure ceratamine A (formula (IIIA); R¹=methyl) (5.4 mg, 0.0116 mmol, 43%) as a yellow solid. The major tautomer was characterized: $^1$H NMR (400 MHz, DMSO) δ 8.68 (m, NH), 7.74 (d, J=9.9 Hz, 1H), 7.66 (s, 2H), 6.42 (d, J=9.9 Hz, 1H), 4.23 (s, 2H), 3.72 (s, 3H), 3.55 (s, 3H), 3.07 (d, J=4.9 Hz, 3H); $^{13}$C NMR (100 MHz, DMSO) δ 175.6, 169.7, 164.1, 160.5, 151.4, 142.9, 140.2, 133.1, 121.3, 116.6, 100.4, 60.3, 43.7, 35.0, 29.2; HRMS (ESI) m/z calcd for $C_{17}H_{17}Br_2N_4O_2$: 466.9713. found: 466.9701. These data from synthetic ceratamine A are consistent with data reported for natural products.

What is claimed is:

1. A method for preparing a compound of the formula (I)

(I)

the method comprising:
dehydrogenating a compound of the formula (II)

(II)

or a salt thereof, with 2-iodoxybenzoic acid in an organic solvent,
wherein
$X^1$ is an aryl hydrocarbon group optionally substituted with one or more groups independently selected from —R, —NH$_2$, —NHR, —NR$_2$, —OH, —OR, —F, —Cl, —Br, —I, —CF$_3$, —C(=O)OH, —C(=O)OR, —C(=O)NH$_2$, —C(=O)NHR, and —C(=O)NR$_2$;
$X^2$ is —H, —R, —NH$_2$, —NHR, —NR$_2$, —OR, —F, —Cl, —Br, or —I; and
R is C$_1$ to C$_{10}$ hydrocarbyl.

2. The method of claim 1, wherein the organic solvent comprises dimethylsulfoxide or a mixture of dimethylsulfoxide and pyridine.

3. The method of claim 1, wherein $X^1$ is a phenyl group of the formula wherein each $X^3$ is independently —H, —F, —Cl, —Br, or —I; and $X^4$ is —H, —CF$_3$, or —OR.

4. The method of claim 3, wherein each $X^3$ is —H and $X^4$ is —H.

5. The method of claim 3, wherein $X^2$ is —NH$_2$, —NHR, or —NR$_2$.

6. A method for preparing a compound of formula (IIIB)

(IIIB)

the method comprising:
dehydrogenating a compound of formula (IV)

(IV)

or a salt thereof, with 2-iodoxybenzoic acid in an organic solvent,
wherein $R^1$ is hydrogen or methyl.

7. The method of claim 6, wherein the organic solvent is selected from the group consisting of dimethylsulfoxide and a mixture of dimethylsulfoxide and pyridine.

8. The method of claim 6, wherein the dehydrogenating comprises:
adding the 2-iodoxybenzoic acid to a reaction mixture comprising the compound of formula (IV) and the organic solvent; and
adding a quenching mixture to the reaction mixture, the quenching mixture comprising a quenching reducing agent and a quenching base in an aqueous solution.

9. The method of claim 6, wherein $R^1$ is methyl, the method further comprising
preparing the compound of formula (IV) or salt thereof according to the steps of reacting a compound of formula (XI)

(XI)

or a salt thereof, with triethyl orthoformate in a methylation mixture; and adding a methylation reducing agent to the methylation mixture to form the compound of formula (IV) or salt thereof in the methylation mixture.

10. The method of claim 9, further comprising preparing a salt of the compound of formula (XI) according to the steps of adding sequentially (i) thiophilic metal salt, (ii) an amine base, and (iii) 1,3-bis(tert-butoxycarbonyl)-2-methyl-2- thiopseudourea to a cooled protection solution comprising a compound of formula (IX)

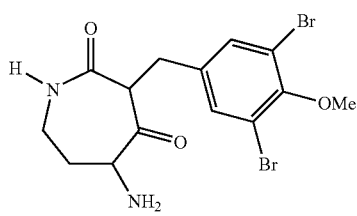

to form a compound of formula (X)

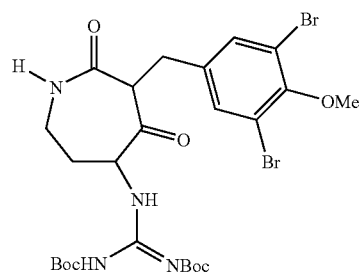

in the cooled protection solution; and
deprotecting the compound of formula (X) with a deprotecting acid to form the salt of the compound of formula (XI).

11. The method of claim 10, wherein the salt of a thiophilic metal is HgCl$_2$.

12. The method of claim 10, wherein the deprotecting acid is trifluoroacetic acid and the deprotecting forms a trifluoroacetate salt of the compound of formula (XI).

13. The method of claim 10, further comprising preparing the compound of formula (IX) according to the steps of
introducing hydrogen gas through a hydrogenation solution, the hydrogenation solution comprising a compound of formula (VIII)

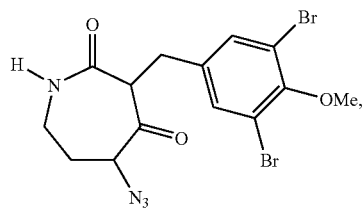

a supported noble-metal catalyst, and a hydrogenation solvent, to form the compound of formula (IX) in the hydrogenation solution.

14. The method of claim 13, further comprising preparing the compound of formula (VIII) according to the steps of brominating a compound of formula (V)

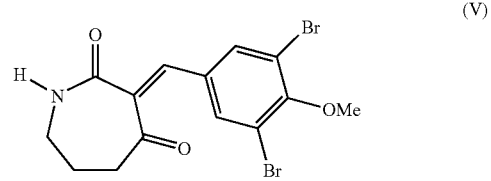

with a bromine source in a bromination solvent to form a compound of formula (VI)

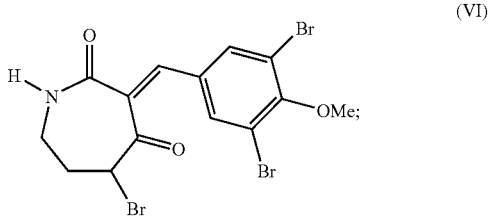

reacting the compound of formula (VI) with Hantzsch ester to form a compound of formula (VII)

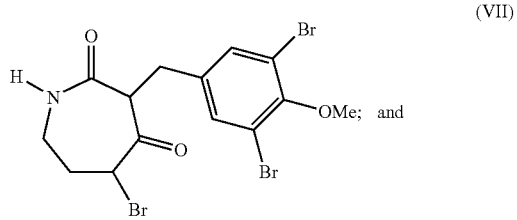

reacting the compound of formula (VII) with an azide source in a polar aprotic solvent to form the compound of formula (VIII).

15. The method of claim 14, further comprising preparing the compound of formula (V) according to the steps of
reacting 4-ethoxy-6,7-dihydro-1H-azepin-2(5H)-one with hydrochloric acid in acetone to form azepane-2,4-dione; and
reacting the azepane-2,4-dione with 3,5-dibromo-4-methoxybenzaldehyde in dichloromethane, acetic acid, and piperidine to form the compound of formula (V).

16. A method for preparing a compound of formula (IIIA)

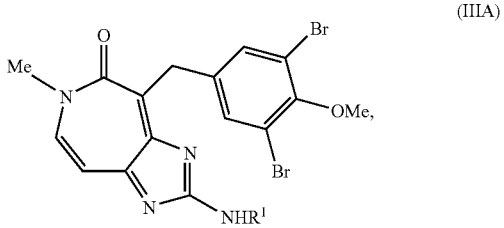

wherein R$^1$ is hydrogen or methyl, the method comprising:
dehydrogenating a compound of formula (IV)

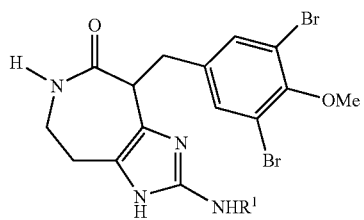

(IV)

or a salt thereof with 2-iodoxybenzoic acid in an organic solvent to form a compound of formula (IIIB)

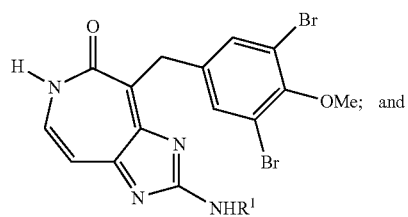

(IIIB)

methylating a lactam nitrogen of the compound of formula (IIIB) to form the compound of formula (IIIA).

17. The method of claim 16, wherein the organic solvent is selected from the group consisting of dimethylsulfoxide or a mixture of dimethylsulfoxide and pyridine.

18. The method of claim 16, wherein the methylating comprises reacting a solution comprising the compound of formula (IIIB) with a methylation agent in the presence of a strong base selected from the group consisting of amide bases and hydride bases.

19. The method of claim 18, wherein the methylation agent comprises iodomethane and the strong base comprises sodium bis(trimethylsilyl)amide.

20. The method of claim 19, wherein the solution comprising the compound of formula (IIIB) further comprises a methylation solvent system comprising dimethylformamide and tetrahydrofuran.

* * * * *